United States Patent
Hakamata et al.

(10) Patent No.: US 7,193,703 B2
(45) Date of Patent: Mar. 20, 2007

(54) SENSOR UNIT FOR ASSAY IN UTILIZING ATTENUATED TOTAL REFLECTION

(75) Inventors: Masashi Hakamata, Kanagawa (JP); Tatsuo Fujikura, Kanagawa (JP)

(73) Assignee: Fuji Photo Film Co. Ltd., Kanagawa (JP)

( * ) Notice: Subject to any disclaimer, the term of this patent is extended or adjusted under 35 U.S.C. 154(b) by 0 days.

(21) Appl. No.: 11/322,350

(22) Filed: Jan. 3, 2006

(65) Prior Publication Data
US 2006/0146333 A1    Jul. 6, 2006

(30) Foreign Application Priority Data
Jan. 4, 2005    (JP) .............................. 2005-000164

(51) Int. Cl.
*G01N 1/10* (2006.01)
(52) U.S. Cl. ..................................................... 356/246
(58) Field of Classification Search ..................... None
See application file for complete search history.

(56) References Cited

U.S. PATENT DOCUMENTS
5,313,264 A    5/1994    Ivarsson et al.

FOREIGN PATENT DOCUMENTS
EP    1 324 019 A1    * 12/2002
JP    3294605 B2    4/2002

* cited by examiner

*Primary Examiner*—Tu T. Nguyen
(74) *Attorney, Agent, or Firm*—Sughrue Mion, PLLC

(57) ABSTRACT

A surface plasmon resonance sensor unit includes a prism. A thin film has a first surface and a sensing surface. The first surface overlies the prism to constitute a thin film/prism interface. The sensing surface immobilizes a sample in sample fluid. Illuminating light is applied to the interface in a form satisfying a condition for total internal reflection, to create attenuated total reflection in the illuminating light reflected by the interface. An angle of incidence of the illuminating light upon the attenuated total reflection is changed upon (bio)chemical reaction of the sample on the sensing surface. The sensor unit includes an enclosing cover, secured to the prism, for covering the sensing surface. A lower recess is formed in the prism, and positioned at the sensing surface. The lower recess constitutes a flow channel for flow of the sample fluid on the sensing surface.

12 Claims, 6 Drawing Sheets

SENSOR UNIT FOR ASSAY IN UTILIZING ATTENUATED TOTAL REFLECTION

BACKGROUND OF THE INVENTION

1. Field of the Invention

The present invention relates to a sensor unit for assay in utilizing attenuated total reflection. More particularly, the present invention relates to a sensor unit for assay in utilizing attenuated total reflection, in which a sensing surface can be positioned precisely relative to a flow channel for flow of a sample fluid.

2. Description of the Related Art

An assay apparatus for assay in utilizing attenuated total reflection is used for various kinds of studies in a biochemical field or the like, for example to study interaction of protein, DNA and various biomaterials, and to select candidate drugs by screening. Also, the technique is useful in the fields of the clinical medicine, food industries and the like.

A surface plasmon resonance (SPR) sensor is known as an assay apparatus in utilizing attenuated total reflection. Surface plasmon is a term to mean the compressional wave created on the surface of the metal and included in plasmon as quantized expression of the compressional wave. Free electrons in a metal vibrate to generate the compressional wave.

U.S. Pat. No. 5,313,264 (corresponding to JP-B 3294605) discloses an SPR assay apparatus in which an optical system of Kretschmann configuration is used for incidence of light to the metal film. According to the Kretschmann configuration, the thin film/dielectric interface of the metal film is fitted on a prism, which condenses light and directs the light to the thin film/dielectric interface in a manner conditioned for total reflection.

Upon the total reflection created on the metal/dielectric interface, a small component of the light passes through the metal film without reflection, and penetrates to the sensing surface. A wave of the penetrating component is called an evanescent wave. Surface plasmon resonance (SPR) is created when frequency of the evanescent wave coincides with that of the surface plasmon. In response to this, intensity of the reflected light attenuates remarkably. In the assay apparatus, the attenuation in the reflected light reflected by the metal/dielectric interface is detected, to recognize creation of the SPR on the sensing surface.

A sample or biomaterial, such as protein and DNA, are handled as sample fluid for the purpose of preventing deactivation or modification due to drying. The sample fluid contains biomaterial and fluid medium, examples of which include pure water, physiological saline water, liquid buffer and the like. U.S. Pat. No. 5,313,264 discloses the assay apparatus for analyzing interaction of the sample. The assay apparatus has a flow channel for flowing and introducing the sample fluid on to a sensing surface. Also, a linker film is overlaid inside the flow channel to have the sensing surface, for immobilizing the sample. Ligand fluid is introduced to the flow channel for immobilizing the ligand on the sensing surface. After this, analyte fluid is introduced for contact of the analyte and the ligand, to assay the interaction between those.

The assay apparatus of U.S. Pat. No. 5,313,264 includes an assay stage where a prism and a flow channel are disposed. A sensor unit of a chip type is positioned on the assay stage for the measuring step, the sensor unit including a glass support and a thin film of metal overlaid thereon.

A problem in the immobilization is in that time required from the introduction of the ligand until completion of the immobilization is as long as one (1) hour or so. This is remarkably longer than the measuring step for the assay which can take only a small number of minutes. As the assay stage of U.S. Pat. No. 5,313,264 is used for both of the sample immobilizing flow and the measuring step for the assay, the assay stage must be occupied for the immobilization during the assay. Other sensor units cannot be set on the assay stage. This is a problem of delay in the operation on the assay stage.

It is conceivable to immobilize samples for all of plural sensor units before assay of those, for the purpose of raising efficiency. However, there is a drawback in that the sensing surface will be dried to deactivate the samples, or will receive impurity stuck thereto, particularly after storing the sensor units with immobilized samples. No assay with precision is possible.

In view of this, an SPR sensor unit is conceived, including a flow channel block, a prism and a retaining block. The flow channel block has a flow channel. The prism is overlaid with a thin film of metal. The retaining block keeps the flow channel block positioned on the prism by setting the flow channel at the thin film.

According to the conception, the flow channel and the prism are provided in the sensor unit itself. The immobilization and the assay are made in simultaneously sequences for plural sensor units, so as to raise efficiency in the operation. Also, the disposition of the flow channel allows preserving of the sensor unit with the sample fluid as storage after the immobilization. Drying of the sensing surface can be prevented.

The flow channel block is formed from rubber or other elastic material for tight contact with the thin film of metal. A retaining block presses the flow channel block against the thin film and kept deformed resiliently. However, the width of the flow channel is as small as one (1) mm. No known technique can eliminate offsetting of the flow channel relative to the sensing surface, because assembly with sufficient precision is extremely difficult.

If the linker film with the sensing surface is offset from the flow channel, an area defined by facing of those changes. Thus, an amount of immobilized ligand changes to influence precision in the measuring step. Enlargement of the linker film may be conceivable in comparison with the flow channel. However, regents or other materials for forming the linker film with the sensing surface are considerably expensive. An unwanted large area of the linker film with the sensing surface is inconsistent to a manufacturing cost which should be reduced to a low level.

SUMMARY OF THE INVENTION

In view of the foregoing problems, an object of the present invention is to provide a sensor unit for assay in utilizing attenuated total reflection, in which a sensing surface can be positioned precisely relative to a flow channel for flow of a sample fluid.

In order to achieve the above and other objects and advantages of this invention, a sensor unit includes a prism, and a thin film having a first surface and a sensing surface, the first surface overlying the prism to constitute a thin film/prism interface, the sensing surface immobilizing a sample in sample fluid provided thereon, wherein illuminating light is applied to the interface in a form satisfying a condition for total internal reflection, to create attenuated total reflection in the illuminating light reflected by the interface, and an incident angle of the illuminating light at which the attenuated total reflection occurs is changed by interaction between the sample and the sensing surface. The sensor unit includes an enclosing cover, secured to the prism, for covering the sensing surface. A recess is formed in at least one of the prism and the enclosing cover, and positioned at the sensing surface. The recess constitutes a flow channel for flow of the sample fluid on the sensing surface in a form closed by securing the enclosing cover to the prism.

Preferably, the recess is formed in the prism, and is provided with the thin film.

Preferably, the flow channel further includes a pair of orifices, formed through the prism and to communicate with the recess.

Preferably, the prism has an upper surface where the pair of orifices are open. A fluid dispenser of a pipetting type is used, and has first and second pipette portions for access to the orifices for one of dispensation and removal of the sample fluid.

Preferably, the flow channel includes an entrance orifice formed to extend from a first end of the recess. An exit orifice is formed to extend from a second end of the recess.

Preferably, the recess is directed downwards from the prism.

Furthermore, a fastener retains the enclosing cover to the prism.

Preferably, the fastener is a type of snap fit fastening.

Preferably, the fastener further includes a retaining hole formed in one of the prism and the enclosing cover. A retaining projection is formed to project from a remaining one of the prism and the enclosing cover, for being retained in the retaining hole.

In one preferred embodiment, the enclosing cover has a cover inner surface positioned opposite to the sensing surface. At least one of the interface and the cover inner surface is disposed inside the recess.

Preferably, the recess is formed in the enclosing cover, and has the cover inner surface.

Furthermore, a positioning recess is formed in one of the prism and the enclosing cover. A positioning projection is formed to project from a remaining one of the prism and the enclosing cover, for being fitted in the positioning recess for positioning.

Preferably, the prism is formed from glass or plastic material.

Preferably, the enclosing cover is formed from glass or plastic material.

Furthermore, a lid is secured to the prism, for covering the orifices. An access hole is formed in the lid, and positioned at the orifices.

Preferably, the lid is attached by adhesive agent to the prism.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
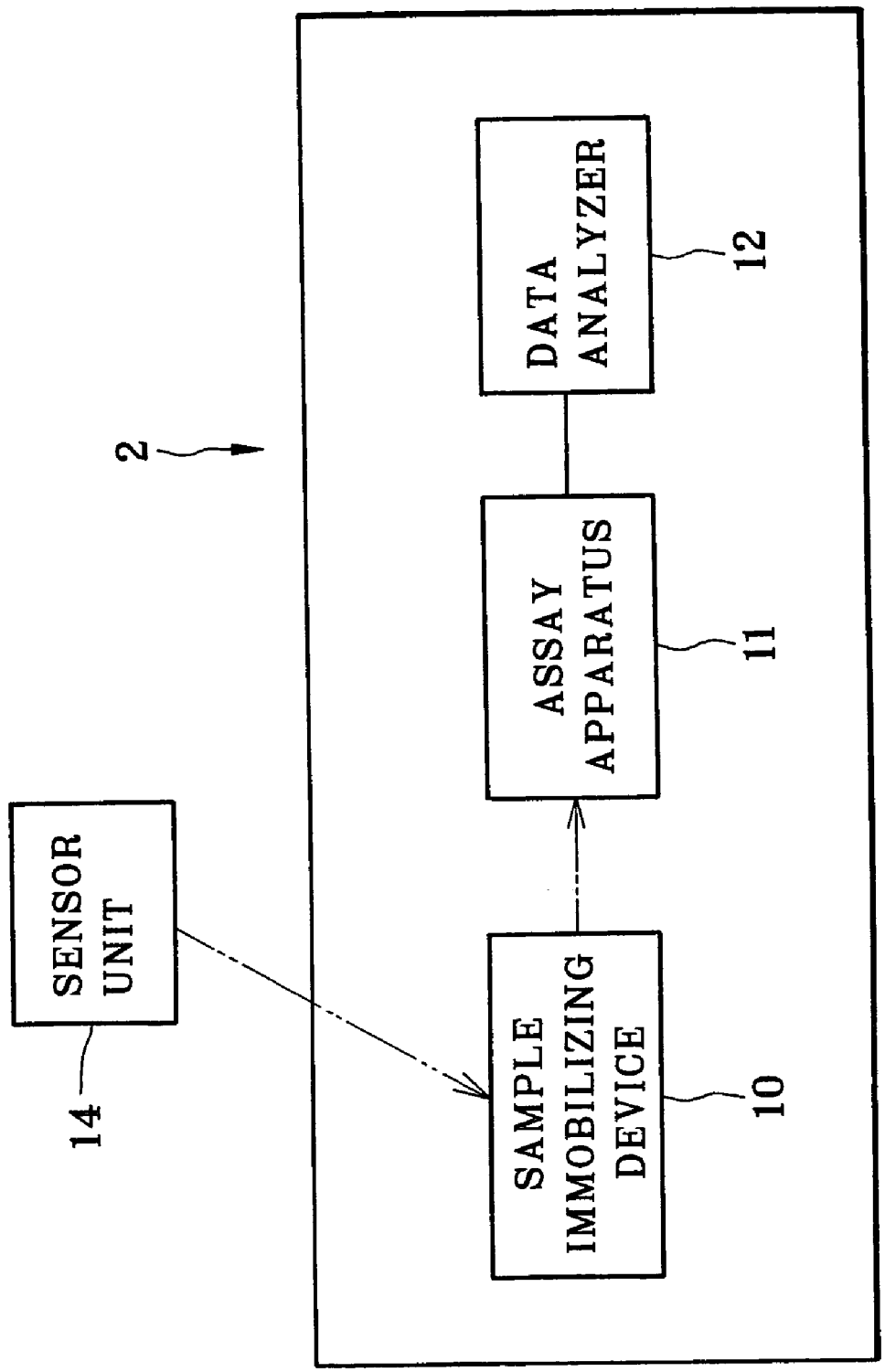
FIG. 1 is a block diagram schematically illustrating an SPR assay system.

In FIG. 1, an SPR (surface plasmon resonance) assay system 2 is schematically illustrated. The assay system 2 includes a sample immobilizing device 10, an assay apparatus 11 and a data analyzer 12.

The sample immobilizing device 10 introduces fluid of ligand toward a sensing surface for the purpose of immobilizing the ligand. The assay apparatus 11 assays interaction between the ligand and an analyte introduced after the ligand immobilization. The data analyzer 12 is provided with data from the assay apparatus 11, and analyzes the data. A sensor unit 14 is separated from any components of the assay system 2, and adapted to operation of a sample immobilizing flow and assay. This can makes it easy to measure a plurality of samples in a rapid manner.

Figure 2:
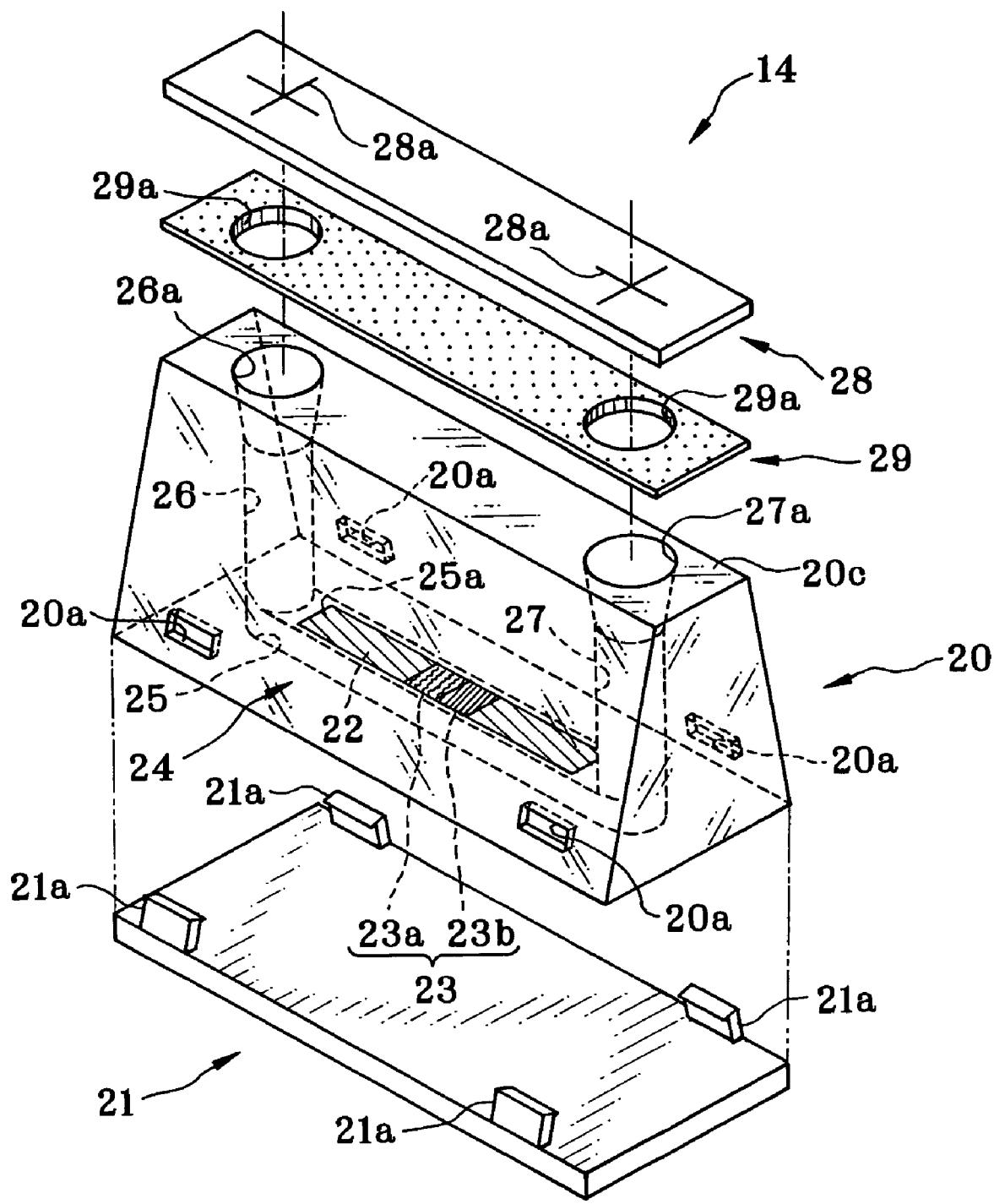
FIG. 2 is an exploded perspective view illustrating a sensor unit.

In FIG. 2, appearance of the sensor unit 14 is illustrated. The sensor unit 14 includes a prism 20, and an enclosing cover 21 disposed under and secured to the prism 20. The prism 20 is formed from a dielectric material and has a metal/dielectric interface.

A lower recess 25 is formed in a lower surface of the prism 20. A thin film 22 of metal is overlaid on the prism 20. A metal/dielectric interface 25a is defined by the thin film 22, and lies inside the lower recess 25. Light incident on the prism 20 is traveled toward the interface 25a, and reflected by the interface 25a by total reflection. The thin film 22 in the reflection causes attenuation of the total reflection. A linker film of a macromolecular material is formed to overlie on the thin film 22. A sensing surface 23 is constituted by the linker film, and adapted to immobilizing ligand or sample of ligand fluid for the purpose of assay. The interface 25a is a total reflection surface or the metal/dielectric interface, on which the prism 20 directs incident light toward the interface 25a.

Various materials can be used for forming the prism 20, their examples including optical glasses, such as borosilicate crown (BK7) glass, barium crown (Bak4) glass, and the like; and optical plastic materials, such as polymethyl methacrylate (PMMA), polycarbonate (PC), amorphous polyolefin (APO) and the like.

An example of material for the thin film 22 is gold (Au) or silver (Ag). A thickness of the thin film 22 is 50 nm. The thickness can be changed for the suitability in view of the material of the thin film 22, a wavelength of light to be applied, and the like. A linker film for the sensing surface 23 is overlaid on a middle portion of the thin film 22 for binding with the ligand. In the manufacturing process of the sensor unit 14, the sensing surface 23 is formed. As the sensing surface 23 is a basis for immobilizing the ligand, a material for the linker film is selectively determined. There are a measuring region 23a (act) and a reference region 23b (ref) formed in the sensing surface 23. The measuring region 23a has immobilization of a ligand, and is a region for reaction between the ligand and analyte. The reference region 23b does not have immobilization of a ligand, and is used for outputting a reference signal for comparison with a signal retrieved from the measuring region 23a. Note that the reference region 23b is formed in the course of film production of the linker film. An example of a process of the forming has steps of surface processing of the sensing surface 23 at first, and then deactivating the reaction groups in approximately a half of an entire area of the sensing surface 23 for binding with ligand. Thus, a half of the sensing surface 23 becomes the measuring region 23a. A remaining half of the sensing surface 23 becomes the reference region 23b.

A flow channel 24 is defined between the prism 20 and the enclosing cover 21, for flow of a sample fluid on to the sensing surface 23 of the linker film, as the enclosing cover 21 closes the lower recess 25 in contact with a lower surface of the prism 20 to cover the thin film 22 and the sensing surface 23. Retaining holes 20a of a fastener are formed in the prism 20. Retaining projections 21a of the fastener are disposed to project from the enclosing cover 21, and engage with the retaining holes 20a for fastening. Note that a different structure may be used. For example, the retaining projections can be formed with the prism 20. The retaining holes can be formed with the enclosing cover 21 for retention of the retaining projections. Also, the retaining holes 20a and the retaining projections 21a can be disposed not on the longer side lines of the enclosing cover 21 but on the shorter side lines of the enclosing cover 21.

Note that it is possible to insert a thin panel of rubber or the like between the prism 20 and the enclosing cover 21, for the purpose of tighten adhesion of those. Also, various materials can be used to form the enclosing cover 21, for example, plastic material, glass, metal or the like. However, a transparent material is preferably used for the data analyzer 12 so as to keep the thin film 22 and fluid observable outside the flow channel 24 through the bottom of the sensor unit.

The flow channel 24 is a U-shaped conduit, and is constituted by the lower recess 25, an entrance zone 26 and an exit zone 27. The lower recess 25 is formed in the prism 20 and closed by the inside of the enclosing cover 21. The entrance zone 26 is a through hole communicating with a first end of the lower recess 25. The exit zone 27 is a through hole communicating with a second end of the lower recess 25. A diameter of the flow channel 24 is approximately 1 mm. A length of the lower recess 25, namely an interval between the entrance zone 26 and the exit zone 27 is approximately 10 mm.

An upper surface 20c lies on the prism 20. An entrance orifice 26a and an exit orifice 27a are formed in the upper surface 20c in respectively a funnel shape. The entrance orifice 26a is connected by the entrance zone 26 with the flow channel 24. The exit orifice 27a is connected by the exit zone 27 with the flow channel 24. A lid 28 is attached to the prism 20 on the upper surface 20c, for preventing evaporation of sample fluid or other fluid in the lower recess 25. To this end, a double-sided adhesive tape 29 with adhesive agent is used for the lid 28. Through holes 29a are formed in the adhesive tape 29, and keep the flow channel 24 accessible through the entrance and exit orifices 26a and 27a.

The lid 28 is formed from rubber, elastomer, resin or other elastic material. A cross shaped access hole or slit 28a is formed in the lid 28 and positioned at each of the entrance and exit orifices 26a and 27a. The cross shaped access slit 28a is formed to enable insertion of pipettes for introduction of fluid into the flow channel 24. When the pipette is externally pulled out, the cross shaped access slit 28a elastically closes the entrance and exit orifices 26a and 27a again by returning to its initial state to prevent liquid in the flow channel 24 from evaporation.

Note that, if the pipettes incidentally contact inner portions upon insertion into the entrance zone 26 and the exit zone 27, breakage is likely to occur by shock on the pipettes, the entrance zone 26 or the exit zone 27 formed respectively from glass. In view of this, it is preferable to form inner portions of the entrance zone 26 and the exit zone 27 with rubber or other elastic material for absorption of shock according to two color injection molding. A material for the two color injection molding is preferably a compound having a small level of non-specific adsorption because adsorption of the sample in the sample fluid should be prevented. An example of a compound with a small level of non-specific adsorption is amorphous polyolefin resins.

Figure 3A:
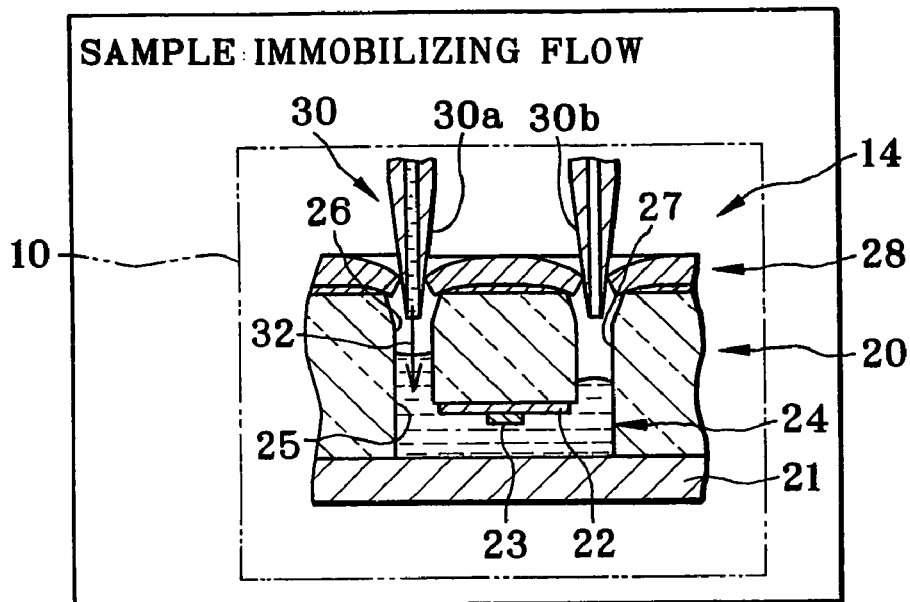
FIG. 3A is an explanatory view in section, illustrating a process of a sample immobilizing flow.
Figure 3B:
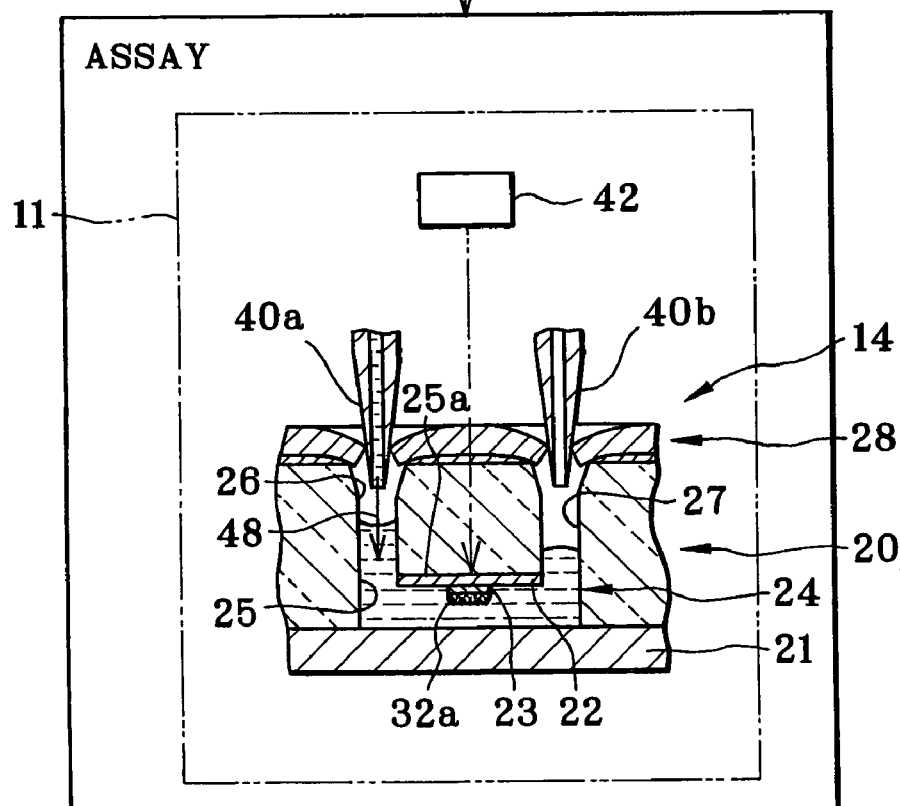
FIG. 3B is an explanatory view in section, illustrating processes of assay and data analysis.

FIGS. 3A and 3B are now referred to for describing assay operation according to the SPR.

A sample immobilizing flow is for binding of ligand on the sensing surface 23 of the linker film. At first, the sensor unit 14 is set in the sample immobilizing device 10. A pipetting type of fluid dispenser 30 is included in the sample immobilizing device 10, and has a dispensing pipette tip 30a and a draining pipette tip 30b. The dispensing pipette tip 30a is set at the entrance orifice 26a. The draining pipette tip 30b is set at the exit orifice 27a. The dispensing pipette tip 30a introduces fluid to the flow channel 24. The draining pipette tip 30b sucks and removes fluid from the flow channel 24. The introduction with the dispensing pipette tip 30a is at the same time as the removal with the draining pipette tip 30b. Ligand fluid 32 as sample fluid, as a fluid which contains ligand or biomaterial and fluid medium, is introduced through the entrance orifice 26a by the fluid dispenser 30.

In the sample immobilizing device 10, pre-treatment before a ligand immobilizing flow with the ligand fluid 32 is wetting of the sensing surface 23 of the linker film by use of liquid buffer, and activation of the sensing surface 23 for the purpose of facilitating binding of the ligand to the sensing surface 23. An example of an immobilizing method is the amine coupling method. An example of material for the linker film is carboxy methyl dextran, to bind an amino group contained in the ligand with the dextran directly by a covalent bond. An example of liquid for the activation is mixture of N'-(3-dimethylaminopropyl) carbodiimide hydrochloride (EDC) and N-hydroxy imide succinate (NHS). The sample immobilizing device 10, after the activation, introduces liquid buffer for the ligand immobilizing flow to wash and clean the flow channel 24.

Various liquids are available for use as the liquid buffer for the ligand immobilizing flow, and solvent or diluent for the ligand fluid 32. Examples of the liquids include buffer liquids, or physiological saline water and other aqueous solutions of physiological salts, and pure water. It is possible according to a type of the ligand to determine suitably solution types and pH values of the solutions, and types of substances to be mixed, and their density. If a biomaterial is used as a ligand, physiological saline water is used of which pH value is kept neutralized. In the amine coupling method described above, the sensing surface 23 of the linker film is electrified negatively because of the carboxy methyl dextran. In consideration of this, it is possible to use phosphate buffered saline (PBS) solution having strong operation of buffer and containing phosphate salt at high density which is not physiological, because protein can be electrified positively for the purpose of facilitating binding with the sensing surface 23.

The sample immobilizing device 10, after the activation and washing, introduces the ligand fluid 32 to the flow channel 24 for immobilization. Ligand 32a as sample such as biomaterial diffused in the ligand fluid 32, in introducing the ligand fluid 32, gradually comes near to and binds with the sensing surface 23 of the linker film. This is ligand immobilizing flow of the ligand 32a on the sensing surface 23. It is general that a step of the immobilization requires approximately one (1) hour, during which the sensor unit 14 is preserved in an environment conditioned suitably, for example at a conditioned temperature. Until the immobilization, the ligand fluid 32 in the flow channel 24 may be left to stand in a stationary state. However, the ligand fluid 32 can be preferably stirred or turbulently flowed for ensured fluidity in the flow channel 24. The stirring or turbulent flow can promote binding of the ligand 32a with the sensing surface 23, to raise an immobilized amount of the ligand 32a.

When the immobilization of the ligand 32a on the sensing surface 23 of the linker film is completed, then the sample immobilizing device 10 removes the ligand fluid 32 from the flow channel 24. Namely, the draining pipette tip 30b discharges the ligand fluid 32 by suction. After this, the sensing surface 23 is washed by introducing washing liquid into the flow channel 24. In the sample immobilizing device 10, a blocking step is made after the washing. A blocking liquid is introduced into the flow channel 24, to deactivate the reaction group remaining without binding with the ligand. A preferable example of the blocking liquid is ethanol amine hydrochloride. After the blocking, the flow channel 24 is washed again. The sample immobilizing device 10 introduces evaporation retardant to the flow channel 24 after the final washing. The sensor unit 14 remains preserved until the assay with the sensing surface 23 humid on the evaporation retardant.

For the process of the assay, the sensor unit 14 is set in the assay apparatus 11. The assay apparatus 11 includes a pipetting type of fluid dispenser 40 and an optical assay unit 42 for surface plasmon resonance. The fluid dispenser 40 is structurally similar to the fluid dispenser 30 in the sample immobilizing device 10. The optical assay unit 42 applies illuminating light to the sensor unit 14, and also measures interaction between the ligand and analyte. A dispensing pipette tip 40a and a draining pipette tip 40b are included in the fluid dispenser 40. The dispensing pipette tip 40a introduces fluids into the flow channel 24 through the entrance orifice 26a.

Figure 4:
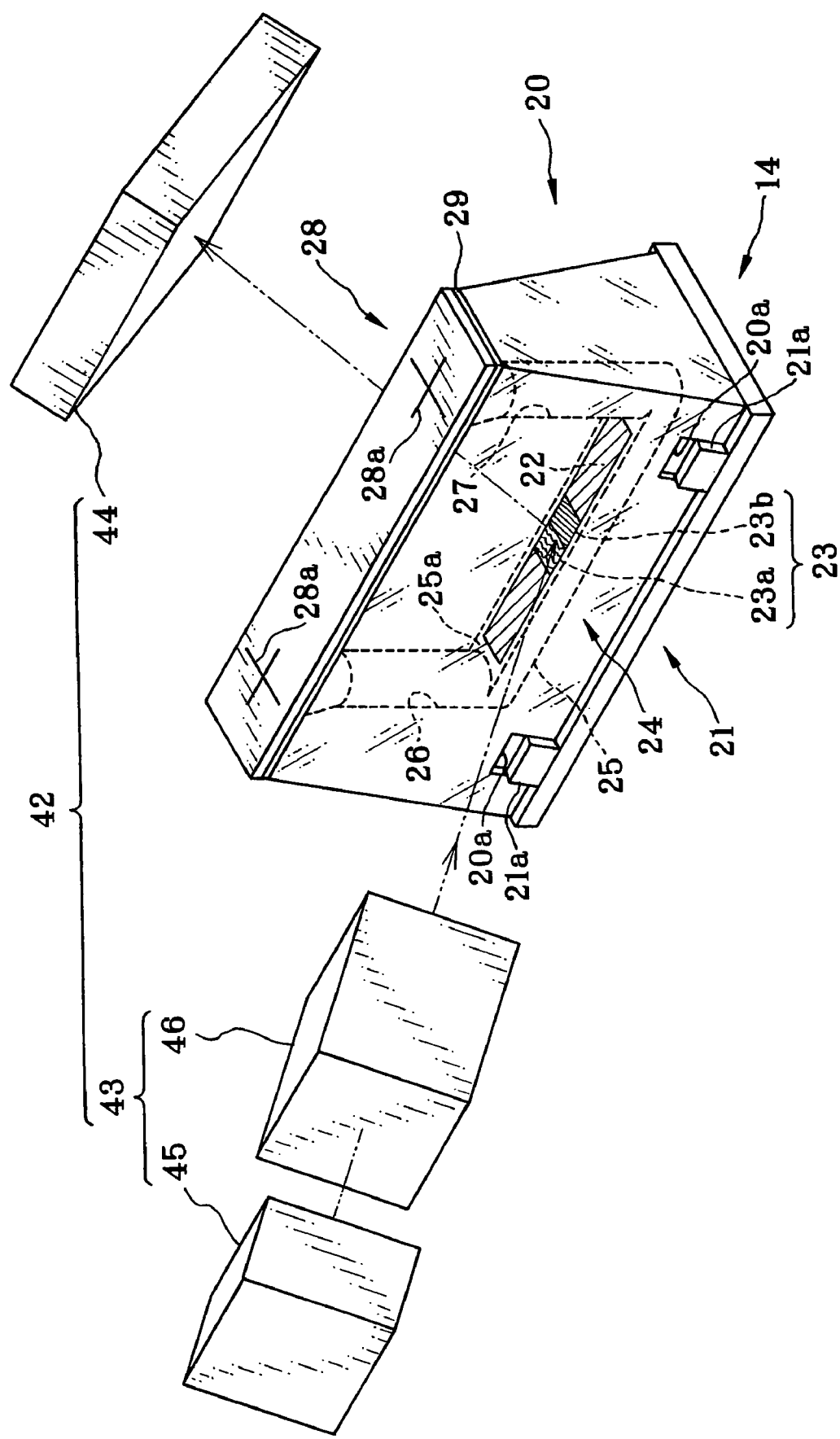
FIG. 4 is a perspective view illustrating an optical assay unit and relevant elements.

In FIG. 4, the optical assay unit 42 is constituted by an illuminator 43 and a photo detector 44. Their arrangement is such that a direction of the illuminating light in the incidence and reflection by the interface 25a is perpendicular to a direction of flow through the flow channel 24.

The illuminator 43 includes a light source device 45 and an illuminating optical system 46, which includes a condensing lens, a diffusing plate and a polarizer. A position and angle of the installation of those elements are so determined that an angle of incidence of the light satisfies the condition of the above total reflection.

Examples of the light source device 45 include a light emitting diode (LED), laser diode (LD), super luminescent diode (SLD), and other light emitting element. A single element is used as the light source device 45 as a point light source, to illuminate the thin film 22. The diffusing plate diffuses light from the light source device 45, and suppresses onset of irregularity in the light amount. The polarizer allows only p-polarized light to pass, the p-polarized light creating the surface plasmon resonance. Note that no polarizer is required if directions of rays emitted by the light source device 45, for example an LD, are kept equal. However, a diffusing plate may be combined with the light source device 45 of a type of which directions of emitted rays are kept equal. Directions of rays in polarization are changed unequal by the passage through the diffusing plate. For this structure, the polarizer can be utilized to set equal the directions of the rays. The light obtained after the diffusion and polarization is condensed by a condensing lens, and directed to the prism 20. It is possible to travel rays with various angles of incidence toward the metal/dielectric interface of the thin film 22 without irregularity in the intensity.

The photo detector 44 receives light reflected by the metal/dielectric interface of the thin film 22, and detects intensity of the light. Rays of light are incident upon the interface of the thin film 22 at various angles. The light is reflected by the interface of the thin film 22 at various angles of reflection according to the angles of the incidence. The photo detector 44 receives the light at various angles of the reflection. An example of the photo detector 44 is a CCD area sensor or an array of photo diodes, which retrieves such a change in the reflection angle as a gradual change in the attenuating position of the reflected light by a photo receptor surface. The photo detector 44 outputs and sends an SPR signal to the data analyzer 12.

The sensing surface 23 of the linker film includes the measuring region 23a and the reference region 23b. On the basis of the measuring region 23a, the photo detector 44 outputs an SPR signal as a measuring signal. On the basis of the reference region 23b, the photo detector 44 outputs an SPR signal as a reference signal.

For the assay, at first, liquid buffer is introduced into the flow channel 24, and caused to flow continuously for a prescribed time. After this, analyte solution or analyte fluid 48, as a fluid which contains analyte and fluid medium that may be solvent, is introduced into the flow channel 24. Then liquid buffer is introduced again. Note that the flow channel 24 may be cleaned or washed before initially introducing the liquid buffer. Reading of data in the photo detector 44 starts upon initially introducing the liquid buffer in order to detect a reference level of a signal. The reading is continued until the introduction of the liquid buffer at the second time after entry of the analyte fluid 48. It is possible not only to detect the reference level but to assay interaction or reaction between the analyte and the ligand, and to measure a signal until dissociation between the analyte and ligand in response to introduction of the liquid buffer.

Various liquids are available for use as the liquid buffer for assay, and solvent or diluent for the analyte fluid 48. Examples of the liquids include buffer liquids, or physiological saline water and other aqueous solutions of physiological salts, and pure water. It is possible according to a type of a ligand or analyte to determine suitably solution types and pH values of the solutions, and types of substances to be mixed, and their density. To facilitate dissolving of the analyte, dimethyl sulfo-oxide (DMSO) can be added to the physiological saline water. The use of the DMSO considerably influences to a level of an output signal. The buffer for assay is used for detecting the reference level of the signal, as described above. If DMSO is contained in the fluid for the analyte, it is preferable to use buffer for assay at a DMSO density approximately equal to that of the fluid in the analyte.

In general, the analyte fluid 48 may be kept preserved for a long time, for example one year. It is likely that a difference occurs between an initial level and a current level of the DMSO density owing to a change with time. If assay with high precision is required, such a difference in the density is estimated according to the reference signal (ref-signal) level upon introducing the analyte fluid 48, so that measured data can be compensated for by DMSO density compensation.

Compensation data for the DMSO density compensation is obtained before introducing the analyte fluid 48. A plurality of liquid buffers different in the DMSO density are introduced to the flow channel 24. Amounts of changes in the levels of ref-signal and act-signal are evaluated so as to obtain the compensation data.

The interaction between the ligand and analyte is recognized as information of shifting of a position of attenuation of the reflected light on the photo reception surface of the photo detector 44. A refraction index of the thin film 22 with the sensing surface 23 of the linker film becomes different between the states before and after the contact of the ligand with the analyte. Thus the resonance angle at which surface plasmon resonance occurs changes between those states. When reaction starts by contact between the analyte and ligand, the resonance angle starts changes, to start shifting the attenuation position of the reflected light on the photo reception surface. A characteristic and other information of the analyte is determined by the assay apparatus 11, which sends the SPR output of the information to the data analyzer 12.

In the data analysis, the SPR signal output by the assay apparatus 11 is analyzed by the data analyzer 12, for quantitatively analyzing characteristics of the analyte. The data analyzer 12 is constituted by a personal computer, workstation or other electronic equipment, and analyzing software installed in such equipment.

The data analyzer 12 effects data analysis by obtaining a difference or ratio of the act-signal and ref-signal output by the assay apparatus 11. For example, the data analyzer 12 obtains data of a finite difference between the act-signal and ref-signal, and analyzes various items according to the finite difference. This makes it possible to cancel electric noise caused by external irregularities, such as individual specificity of the sensor unit 14 or the sensing surface 23 of the linker film, mechanical changes of the assay apparatus 11, temperature changes of the liquid, and the like. A signal with a high S/N ratio can be obtained.

The operation of the sensor unit 14 constructed above is described now. The sensor unit 14 includes the prism 20 and the enclosing cover 21. The prism 20 is provided with the enclosing cover 21 attached thereto, so as to define the flow channel 24 by closing the lower recess 25.

It is possible according to the invention that the flow channel 24 can be reliably positioned on the sensing surface 23 of the linker film in the sensor unit 14 without offsetting, because the thin film 22 and the sensing surface 23 are formed inside the lower recess 25 constituting the flow channel 24 at the interface 25a.

In a conventionally used sensor, a flow channel block is incorporated as an element formed from rubber or other elastic material. If the elastic block is pressed irregularly, a shape viewed in the section in the flow channel will change, to lower the precision in the measurement. However, the sensor unit 14 in the invention is formed from elements of glass, plastic material or other rigid materials, including the prism 20 and the enclosing cover 21. Thus, no deformation of the shape of the flow channel 24 as viewed in section takes place. Precision in the assay can be high.

Also, a flow channel block, used in the known sensor unit in the field of SPR, is not used in the present invention. This is advantageous in reducing the number of parts of a sensor unit. No extra large area of the sensing surface 23 of the linker film is required. Positioning of the sensing surface 23 on the flow channel 24 can be made with high precision also at a low cost.

In the above embodiment, the fastener is constituted by the retaining holes 20a and the retaining projections 21a combined in a snap fit fastening. However, any suitable elements may be used instead, for example fastening of screws, adhesive agent, and the like. A preferable adhesive agent is a non-volatile adhesive agent, because evaporation of the solvent causes the adhesive agent to influence the thin film 22 or the sensing surface 23 of the linker film. Also, any one of the sample immobilizing device 10 and the assay apparatus 11 has a pressure mechanism for keeping the prism 20 in tight contact with the enclosing cover 21. This is favorable instead of the fastener for various steps for the purpose of SPR assay.

In the above embodiment, the enclosing cover 21 is as large as a lower surface of the prism 20. However, the enclosing cover 21 can be formed in any suitable shape to enclose the lower recess 25, for example may be a bar-like panel shape that is long in one direction, or in a shape of a triangular prism.

In the above embodiment, the entrance zone 26 and the exit zone 27 extend to the lower recess 25. However, a single orifice or zone can be formed and used for dispensation and drainage. Furthermore, three or more orifices or zones may be formed. Also, no orifice or zone may be extended to the lower recess 25. The lower recess 25 can be formed to extend straight in a through shape, to form a linear shape of the flow channel 24.

In the above embodiment the lower recess 25 is formed in the prism 20. Instead, the lower recess 25 can be formed in the enclosing cover 21 as illustrated in FIGS. 5 and 6.

In relation of the positioning, the lower recess 25 is set at the sensing surface 23 of the linker film in a normal manner without specific precision in the shape of the lower recess 25 formed in the enclosing cover 21. However, the prism 20 and the enclosing cover 21 can have high rigidity owing to the use of glass, plastic material or other hard material. The positioning of the lower recess 25 at the sensing surface 23 depends solely upon mechanical precision. Machining of mechanical elements widely used today is considerable precise. It is reliably possible to prevent offsetting between the sensing surface 23 and the flow channel 24, because variable components due to the use of elastic material is eliminated in the present invention.

Figure 5:
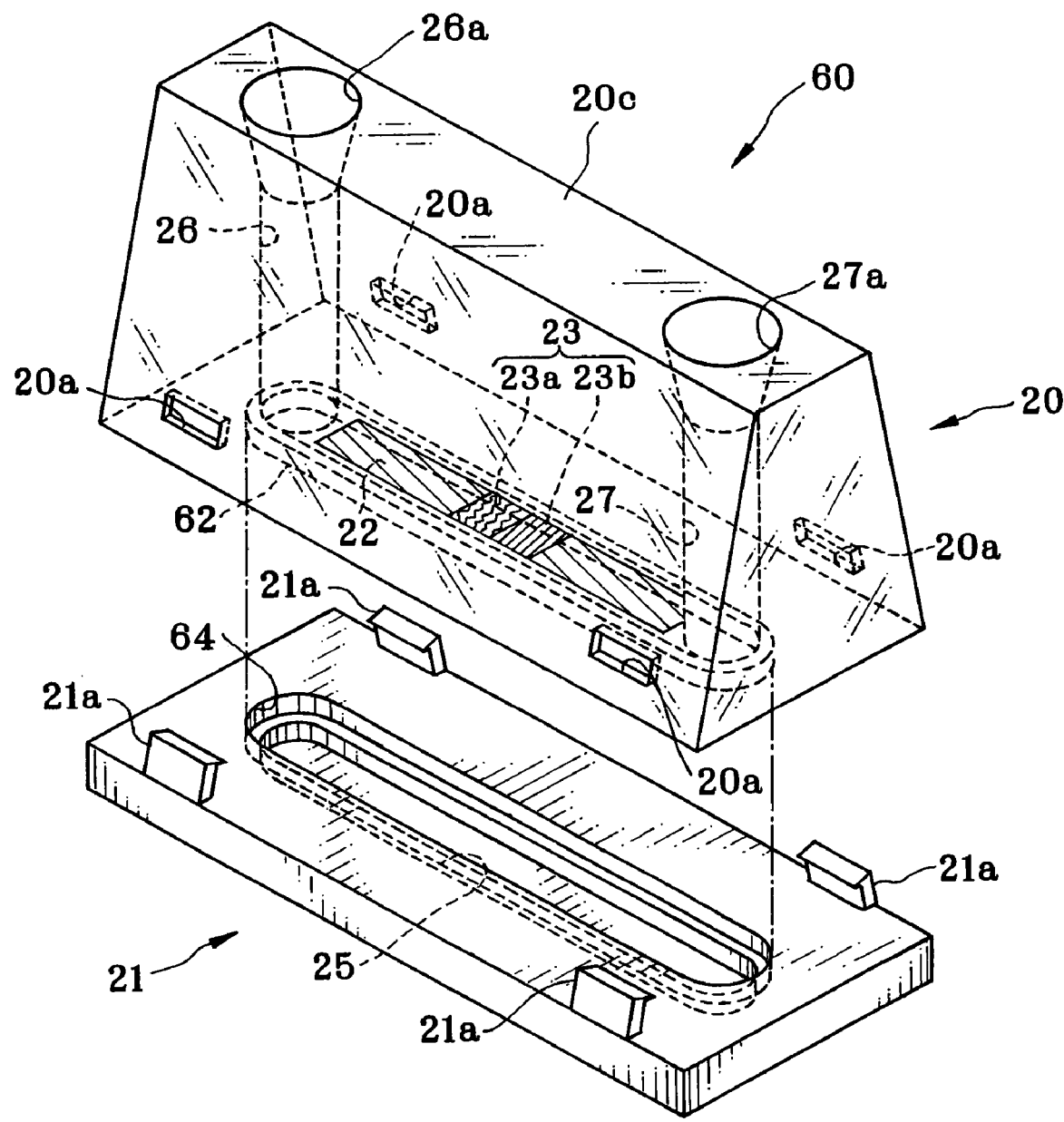
FIG. 5 is an exploded perspective view illustrating another preferred sensor unit.
Figure 6:
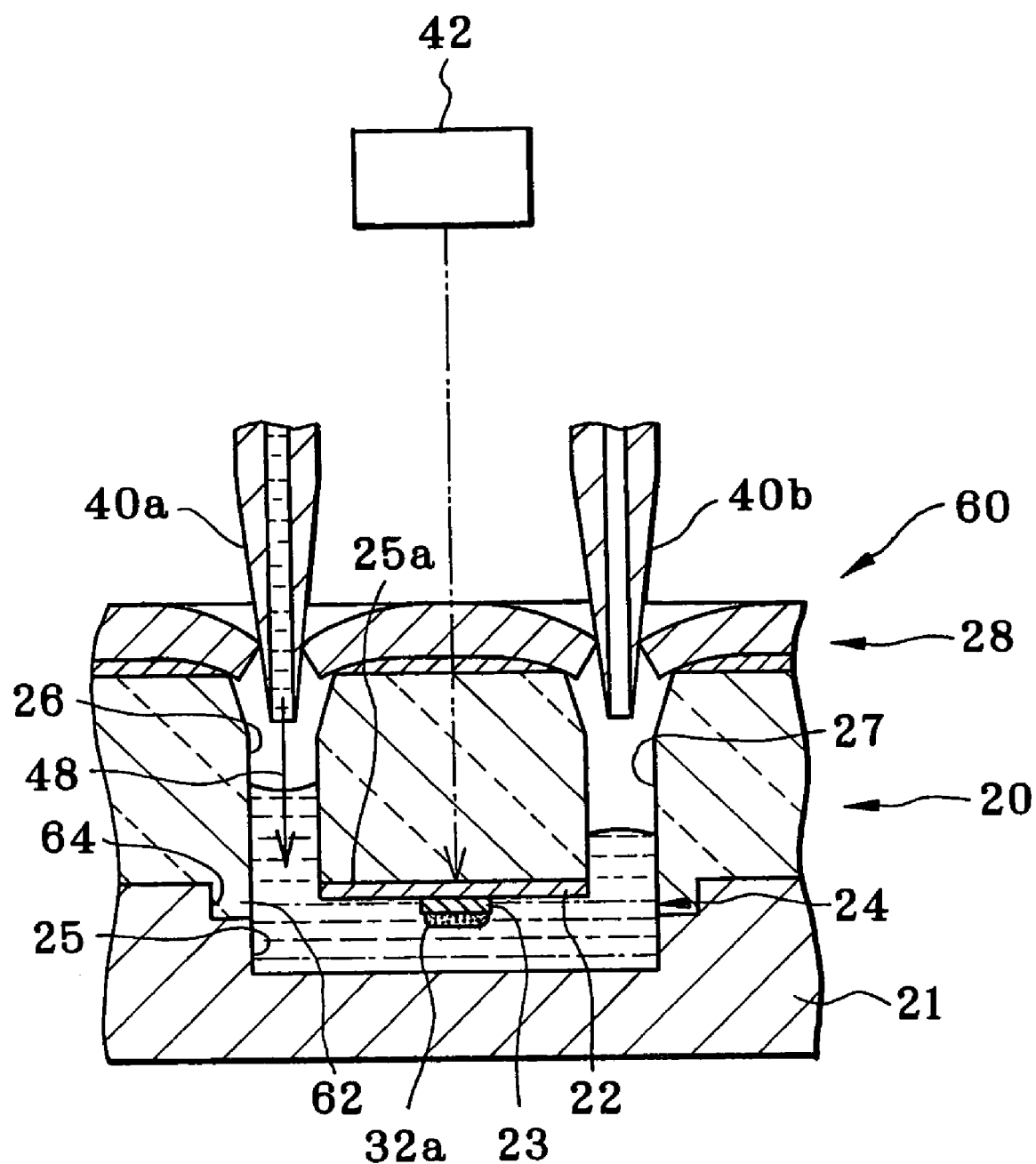
FIG. 6 is an explanatory view in section, illustrating the sensor unit of FIG. 5.

In FIGS. 5 and 6, a loop-shaped positioning ridge 62 is preferably formed to project from the prism 20 to extend about a position of the flow channel 24. An edge positioning recess 64 is formed in the enclosing cover 21 and engageable with the positioning ridge 62. Thus, offsetting between the sensing surface 23 of the linker film and the flow channel 24 can be prevented even with the lower recess 25 formed in the enclosing cover 21. The flow channel 24 can be kept enclosed in a water-tight state.

Any of a sensor unit 60 of the second embodiment and the sensor unit 14 has the sensing surface 23 of the linker film and the flow channel 24 as one combination. However, the sensor unit 14 or 60 according to the invention may be a multi channel sensor unit including a plurality of the sensing surfaces 23 and a plurality of the flow channels 24. The prism 20 and the enclosing cover 21 can have a shape prolonged in their longitudinal direction. Furthermore, the sensor unit 14 or 60 can be a sensor module removably connected with one another by use of connecting mechanisms. This is effective in a wide use of the sensor unit 14 or 60 in both of the single channel sensor unit and the multi channel sensor unit even with a simple structure. Note that, if the prism 20 and the enclosing cover 21 are formed considerably longer than depicted, the retaining holes 20a and the retaining projections 21a should be preferably arranged one after another on the longer side lines. See FIGS. 2, 4 and 5. The plural arrangement can prevent curving of the enclosing cover 21.

In addition to the SPR sensor, an assay sensor unit according to the invention can be other sensor in utilizing attenuated total reflection. One example of sensor unit according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a metal/dielectric interface on the cladding layer. When light becomes incident on the metal/dielectric interface to satisfy the condition of the total reflection, part of the light passes through the cladding layer, and enters the optical waveguide layer. A guided mode to propagate light is excited responsively in the optical waveguide layer, to attenuate the reflected light on the metal/dielectric interface. An angle of the incidence at which the guided mode is excited is changeable according to the refraction index of the medium positioned on the sensing surface. This is similar to the characteristic of the resonance angle of the SPR sensor. The attenuation of the reflected light is detected, so that it possible to measure the interaction on the sensing surface.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A sensor unit, including a prism, and a thin film having a first surface and a sensing surface, said first surface overlying said prism to constitute a thin film/prism interface, said sensing surface immobilizing a sample in sample fluid provided thereon, wherein illuminating light is applied to said interface in a form satisfying a condition for total internal reflection, to create attenuated total reflection in said illuminating light reflected by said interface, and an incident angle of said illuminating light at which said attenuated total reflection occurs is changed by interaction between said sample and said sensing surface, said sensor unit comprising:

an enclosing cover, secured to said prism, for covering said sensing surface;
a recess, formed in at least one of said prism and said enclosing cover, and positioned at said sensing surface;
said recess constituting a flow channel extending through said prism for flow of said sample fluid on said sensing surface in a form closed by securing said enclosing cover to said prism.

2. A sensor unit as defined in claim 1, wherein said recess is formed in said prism, and is provided with said thin film.

3. A sensor unit as defined in claim 2, further comprising a fastener for retaining said enclosing cover to said prism.

4. A sensor unit as defined in claim 3, wherein said fastener is a type of snap fit fastening.

5. A sensor unit as defined in claim 1, wherein said flow channel has a pair of orifices for dispensing and removing said sample fluid, and said orifices are connected with ends of said recess and extend through said prism.

6. A sensor unit as defined in claim 5, where said pair of said orifices include an entrance orifice for dispensation and an exit orifice for removal.

7. A sensor unit as defined in claim 1, wherein at least one of said prism and said enclosing cover is formed from glass or plastic material.

8. A sensor unit as defined in claim 1, wherein said recess is formed in said enclosing cover.

9. A sensor unit as defined in claim 8, further comprising:
a positioning recess formed in one of said prism and said enclosing cover; and
a positioning projection, formed to project from said prism or said enclosing cover without the positioning recess, for being fitted in said positioning recess for positioning said recess at said sensing surface.

10. A sensor unit as defined in claim 9, wherein at least one of said prism and said enclosing cover is formed from glass or plastic material.

11. A sensor unit, including a prism, and a thin film having a first surface and a sensing surface, said first surface overlying said prism to constitute a thin film/prism interface, said sensing surface immobilizing a sample in sample fluid provided thereon, wherein illuminating light is applied to said interface in a form satisfying a condition for total internal reflection, to create attenuated total reflection in said illuminating light reflected by said interface, and an incident angle of said illuminating light at which said attenuated total reflection occurs is changed by interaction between said sample and said sensing surface, said sensor unit comprising:

an enclosing cover, secured to said prism for covering said sensing surface;
a recess, formed in at least one of said prism and said enclosing cover, and positioned at said sensing surface; and
a fastener for retaining said enclosing cover to said prism comprising:
a retaining hole formed in one of said prism and said enclosing cover; and
a retaining projection, formed to project from a remaining one of said prism and said enclosing cover, for being retained in said retaining hole;
said recess constituting a flow channel for flow of said sample fluid on said sensing surface in a form closed by securing said enclosing cover to said prism;
wherein said recess is formed in said prism and is provided with said thin film.

12. A sensor unit, including a prism, and a thin film having a first surface and a sensing surface, said first surface overlying said prism to constitute a thin film/prism interface, said sensing surface immobilizing a sample in sample fluid provided thereon, wherein illuminating light is applied to said interface in a form satisfying a condition for total internal reflection, to create attenuated total reflection in said illuminating light reflected by said interface, and an incident angle of said illuminating light at which said attenuated total reflection occurs is changed by interaction between said sample and said sensing surface, said sensor unit comprising:

an enclosing cover, secured to said prism, for covering said sensing surface;
a recess, formed in at least one of said prism and said enclosing cover, and positioned at said sensing surface;

said recess constituting a flow channel for flow of said sample fluid on said sensing surface in a form closed by securing said enclosing cover to said prism; and wherein said flow channel has a pair of orifices for dispensing and removing said sample fluid, and said orifices are connected with ends of said recess and extend through said prism;

a lid, secured to said prism, for covering said orifices; and an access hole, formed in said lid, and positioned at said orifices, adapted to access of a fluid dispenser of a pipetting type, to dispense or remove said sample fluid.

* * * * *